United States Patent [19]
Larsen et al.

[11] Patent Number: 5,302,023
[45] Date of Patent: Apr. 12, 1994

[54] LOCALIZED CONVECTION ENVIRONMENTAL CHAMBER

[75] Inventors: Carl G. Larsen; Bryon J. Saari, both of Minneapolis, Minn.

[73] Assignee: MTS Systems Corporation, Eden Prairie, Minn.

[21] Appl. No.: 876,362

[22] Filed: Apr. 30, 1992

[51] Int. Cl.⁵ .............................................. G01N 25/00
[52] U.S. Cl. ...................................................... 374/46
[58] Field of Search ................. 73/788, 826, 828, 830, 73/834; 219/201; 392/347, 349, 350, 360, 635, 368, 369; 374/45-52, 57

[56] References Cited

U.S. PATENT DOCUMENTS

| | | | |
|---|---|---|---|
| 2,154,280 | 4/1939 | Nadai et al. | 374/49 |
| 2,579,424 | 12/1951 | Gehman | 374/46 |
| 2,904,993 | 9/1959 | Grover et al. | 374/49 |
| 3,492,862 | 2/1970 | Wallace | 73/834 |
| 4,537,080 | 8/1985 | Christiansen | 73/857 |
| 4,549,072 | 10/1985 | Brist et al. | 392/365 |
| 4,711,587 | 12/1987 | Cocito . | |

FOREIGN PATENT DOCUMENTS

| | | | |
|---|---|---|---|
| 0099331 | 6/1984 | Japan | 374/46 |
| 0178334 | 9/1985 | Japan | 374/49 |
| 164694 | 8/1964 | U.S.S.R. | 374/46 |
| 361418 | 12/1972 | U.S.S.R. | 374/46 |

OTHER PUBLICATIONS

MTS Specification Sheet No. 651.04, Series 651 Environmental Chambers.
MTS Application Notes, Model 657.03 High Temperature Furnace.
MTS Specification Sheet No. 657.02, Model 657.02 High Temperature Furnace.

*Primary Examiner*—Robert Raevis
*Attorney, Agent, or Firm*—Westman, Champlin & Kelly

[57] ABSTRACT

A gas convection assembly is disclosed for maintaining a desired temperature gradient on a test portion of a test specimen. The assembly includes a housing having a chamber defined by bounding walls. The chamber is accessible through apertures in the housing. The housing is positioned relative to the test specimen such that the apertures are substantially aligned along a longitudinal axis of the test specimen with the test portion located in the chamber and end portions of the test specimen that extend out the apertures. A fan is provided to force gas into the chamber to heat or cool the test portion.

20 Claims, 4 Drawing Sheets

LOCALIZED CONVECTION ENVIRONMENTAL CHAMBER

BACKGROUND OF THE INVENTION

The present invention relates to environmental chambers that are used to control the environment surrounding a test specimen. More particularly, the present invention provides a gaseous convection environmental chamber that heats or cools a limited portion of the test specimen.

Commonly, during the testing of material specimens, for example, such as tensile and compressive loading, the specimen to be tested is placed in an environmental chamber. The environmental chamber controls or modifies the environment surrounding the test specimen, and thus, the condition of the specimen itself. By controlling environmental parameters such as temperature and humidity, operating conditions can be simulated in order to determine accurately the performance of the tested material.

Three common techniques are used in environmental chambers to alter the temperature of the test specimen. These techniques include the use of radiant heat energy, induction heat energy, or forced gas or convection heat energy. Briefly, induction heating is the heating of an electrically conducting material by eddy currents induced by a varying electromagnetic field. Radiant heating uses a heat-producing surface that emits heat to the test specimen by radiation rather than by conduction or convection. Environmental chambers that incorporate radiant heating to alter the temperature of a given test specimen include a housing that surrounds either the complete test specimen and the test specimen holding assemblies, or alternatively, a housing that surrounds only a portion of the test specimen. In both forms of radiant heating systems, the radiant heating elements are positioned adjacent the test specimen or a portion thereof in the environmental chamber to localize energy upon the test specimen. Radiant heating, like induction heating, is well suited for heating the test specimen to high temperatures, but neither technique will cool a test specimen to a temperature below the ambient temperature.

In contrast, convection systems are commonly used to either raise and lower the temperature of the test material above or below the ambient temperature. In these known systems, a convection environmental chamber includes a housing that surrounds the test specimen and the test specimen holding assemblies. A fan then moves a gaseous medium, such as air, from a heating or cooling source to the test specimen to obtain the desired operating temperature.

Drawbacks to this type of convection environmental chamber however exist. The most serious drawback is that since the housing surrounds both the test specimen and the test specimen holding assemblies, the test specimen holding assemblies are subjected to the same environment as the test specimen. When high operating temperatures are desired on the test specimen, the standard holding assemblies must be replaced with high temperature holding assemblies manufactured from special alloys and/or equipped with cooling jackets. In either case however, these high temperature holding assemblies are substantially more expensive than the standard holding assemblies, and thus increase the cost associated with testing.

SUMMARY OF THE INVENTION

The present invention relates to a gas convection assembly or environmental chamber for maintaining a desired temperature on a test portion of a test specimen. The test specimen is mounted at opposite ends along its longitudinal axis on support members (grips) during testing of the test specimen. The environmental chamber comprises a housing having a chamber defined by an upper wall, a lower wall, and side walls extending between the upper and lower walls. The chamber is provided with aligning apertures in the housing. The housing is positioned relative to the test specimen such that the apertures are substantially centered on the specimen's longitudinal axis with a control test portion of the specimen located in the chamber, while end portions of the test specimen extend out the apertures.

A fan is connected to the housing for forcing a gas into the chamber. The gas maintains the test portion of the test specimen at the desired temperature.

In a preferred embodiment, a baffle is connected between the fan and the test portion to control or adjust the velocity of the gas striking or flowing past areas of the test portion. By adjusting the velocity of the forced gas, the natural temperature gradients that can exist between center portions and end portions of test specimen are compensated to obtain a desired temperature gradient, which is less than the uncompensated temperature gradient, and which gradient, optimally, approaches zero.

The present invention provides an improved convection environmental chamber. The present invention heats or cools only the desired test portion of the test specimen by providing a housing that maximizes the available space between the grip assemblies, while minimizing the temperature gradient along the test portion. Furthermore, since the grips are not located inside the housing but rather outside the housing, expensive, special grips are not required. Instead, standard grips can be used, thereby realizing substantial savings in the cost associated with testing materials.

DETAILED DESCRIPTION OF THE PREFERRED EMBODIMENTS

Figure 1:
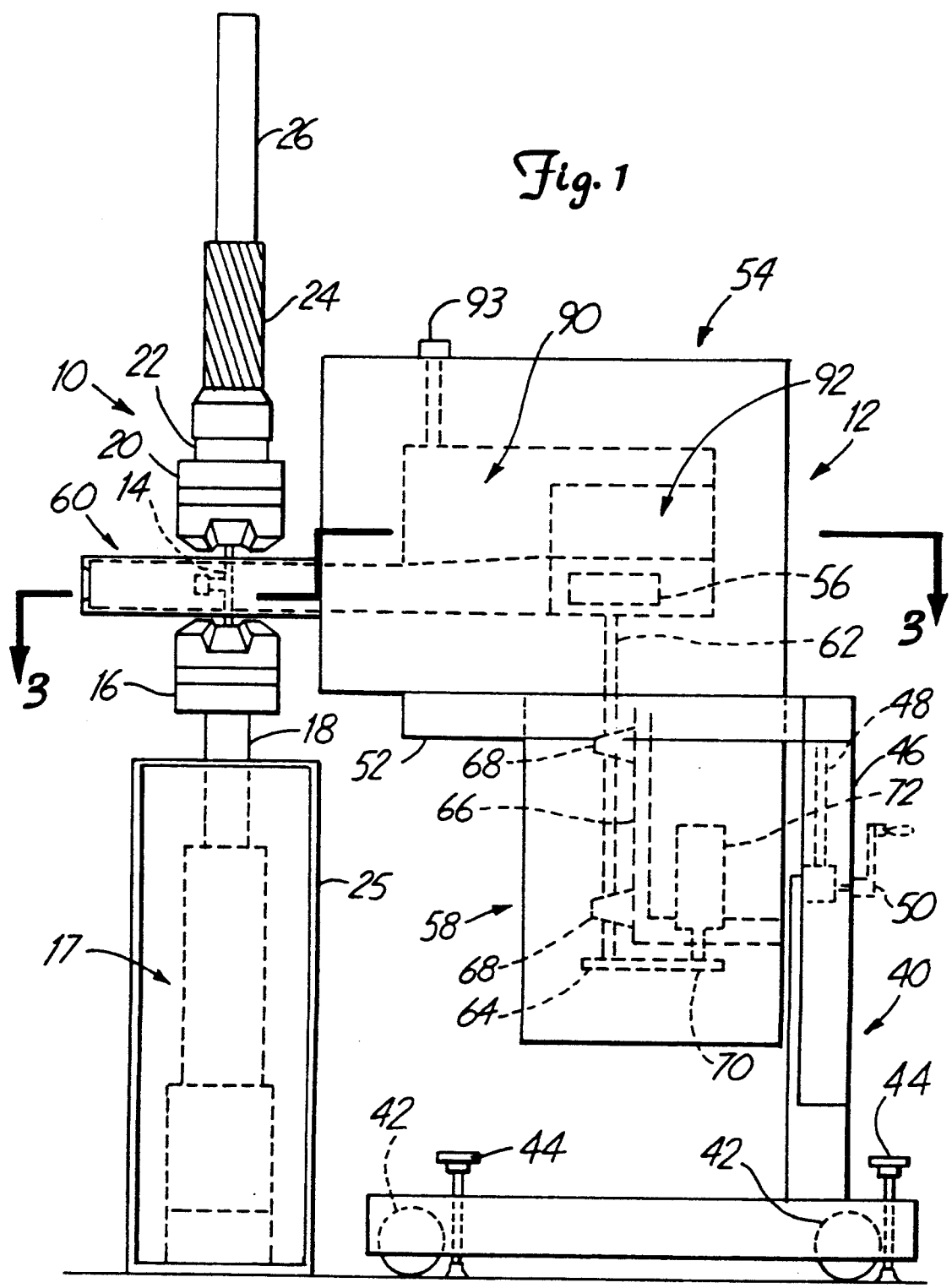
FIG. 1 is a side elevational view of an environmental chamber of the present invention.
Figure 3:
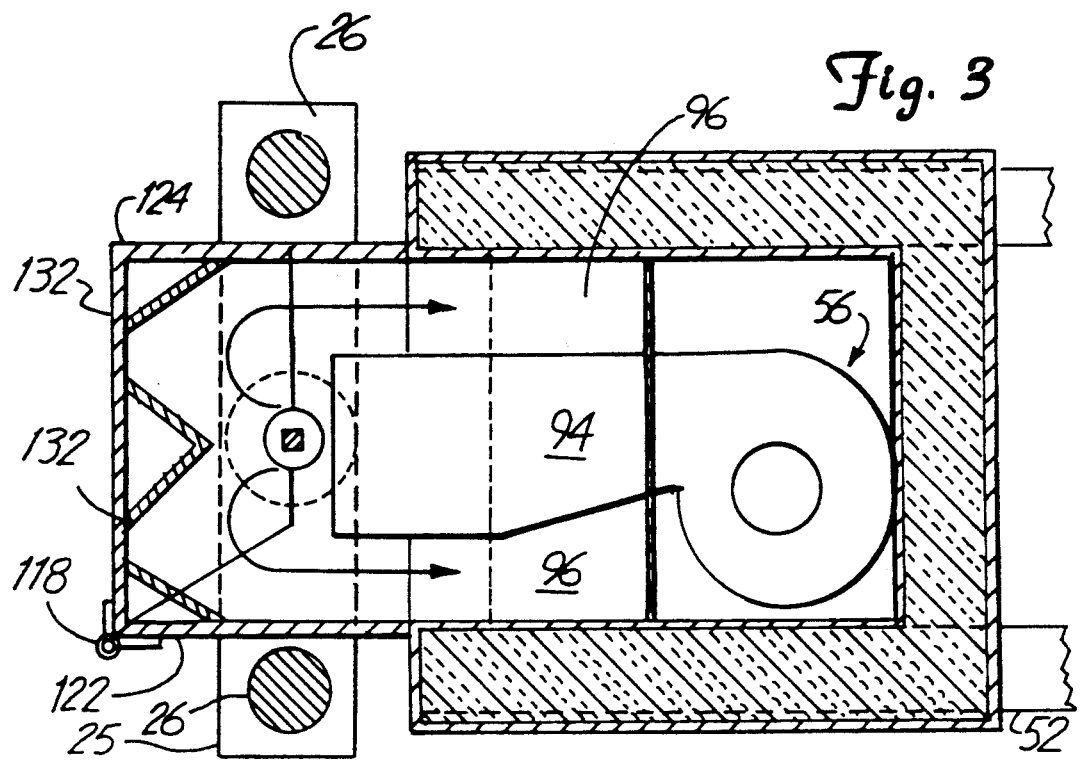
FIG. 3 is a sectional view of the environmental chamber taken as on line 3—3 of FIG. 1.

FIG. 1 illustrates a tension and compression testing system generally at 10, and a convection environmental chamber of the present invention generally at 12. The tension and compression testing system 10 loads a test specimen 14 along a longitudinal axis thereof through test specimen holding assemblies or grips. A lower grip 16 is connected to an actuator 17 located in a base 25 of the testing system 10 through a piston rod 18. An upper grip 20 is connected through a rod to force measuring load cell 22, which is connected to a support member 24 that is fixed in position during loading but is longitudinally slidably adjustable along the longitudinal axis on support columns 26,26, illustrated in FIG. 3, to accommodate test specimens of different lengths. The support columns 26,26 are secured to the base 25. The upper and lower grips hold the test specimen 14 along its longitudinal axis while the actuator 17 applies tension, compression, or alternating tension and compression loading to the test specimen 14.

Figure 2:
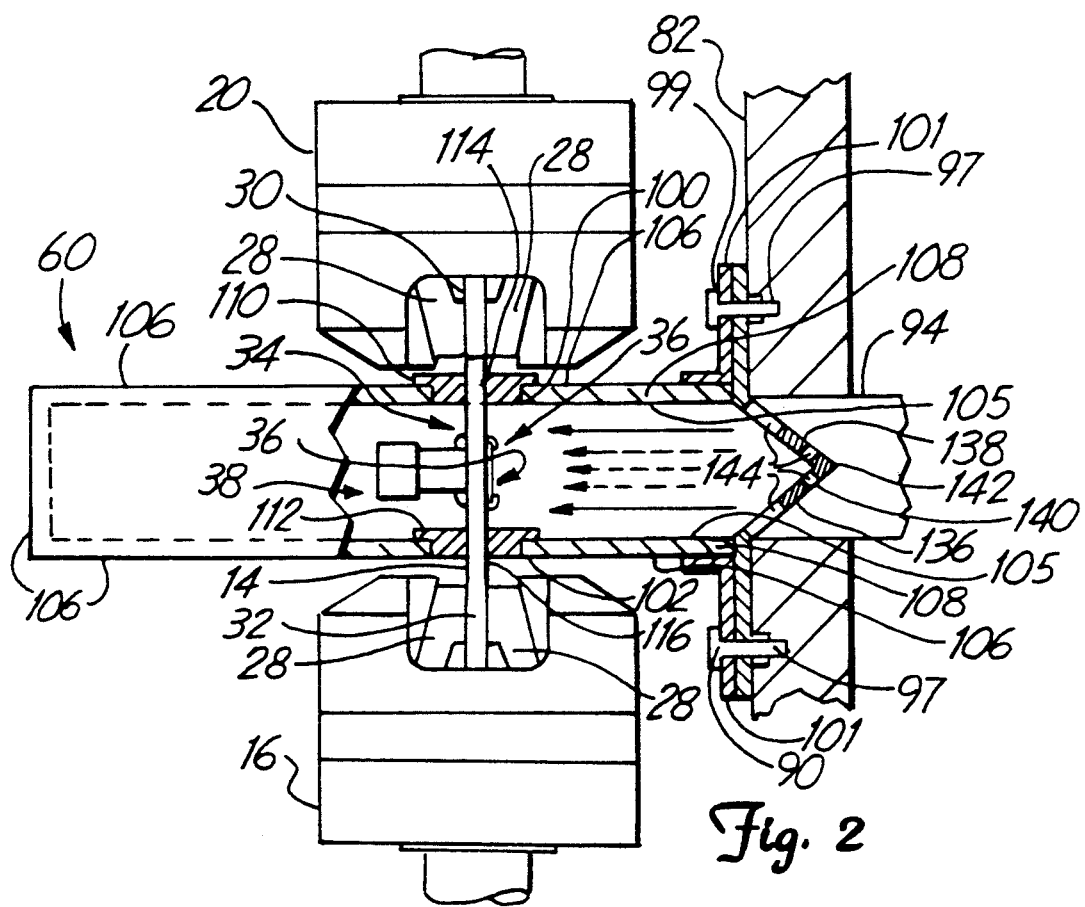
FIG. 2 is an enlargement of FIG. 1 showing a test chamber housing in detail.

The upper grip 20 and the lower grip 16 are similar to that shown in U.S. Pat. No. 4,537,080 issued to Christiansen and assigned to the same assignee as the present invention. Referring to FIG. 2, the grips 16 and 20 are hydraulically actuated with opposed clamping jaws 28,28 that grip end portions 30 and 32 of the test specimen 14 whereby a control test portion 34, joined to each end portion 30 and 32, is positioned within a chamber 36. When a high temperature environment is desired for the test portion 34 which would result in undesirable temperature increases in the grip jaws 28,28, due to thermal conduction of heat from the test portion 14 through each end portion 30 and 32 and to the jaws 28,28, the upper and lower grips may include conventional water cooling to cool the grip jaws 28,28.

As illustrated in FIG. 2, material performance is measured via a suitable sensor 38. The sensor 38, such as an extensometer, is conventionally mounted to the test portion 34 and measures length changes of the test portion (strain) due to force loading on the test specimen 14, particularly that loading present on the test portion 34.

Referring back to FIG. 1, the environmental chamber 12 of the present invention is mounted to a movable cart 40 having casters or wheels 42 for positioning the chamber 12 adjacent to the force loading test system 10. Leveling feet 44 are provided to secure the position of the cart 40 and chamber 12 adjacent to the test system 10 as well as to permit adjusting or leveling the chamber 12 with respect to the test system 10. A vertical support 46 of the cart 40 includes a lift 48 having a crank 50 to adjust the vertical placement of the chamber 12 relative to the test specimen 14. The chamber 12 is mounted to a horizontal support 52 of the cart 40 and includes a fan section indicated generally at 54, having a fan 56, a drive section indicated generally at 58 to drive the fan 56, and a test chamber housing 60 to receive the forced gas from the fan 56. Although described hereinafter with the gaseous medium being air, it is understood that the present invention is equally suited for other types of gases.

The drive section 58 is substantially thermally isolated from the fan section 54 through a drive shaft 62. The fan 56 is mounted to an end of the drive shaft 62, while a drive pulley 64 is mounted at an opposite end. The drive shaft 62 is supported on a vertical support 66 with bearings 68 allowing rotation of the drive shaft 62. The drive pulley 64 is connected to a motor pulley 70, which in turn is connected to a conventional motor 72. The drive pulley 64 is an adjustable sheave that permits adjusting its effective diameter, and thus the rotational speed of the drive shaft 62 and fan 56, which in turn controls the average velocity of air flow from the fan 56. Alternatively, the adjustable sheaves can be eliminated and a variable frequency motor can be installed to control average air velocity.

Figure 4:
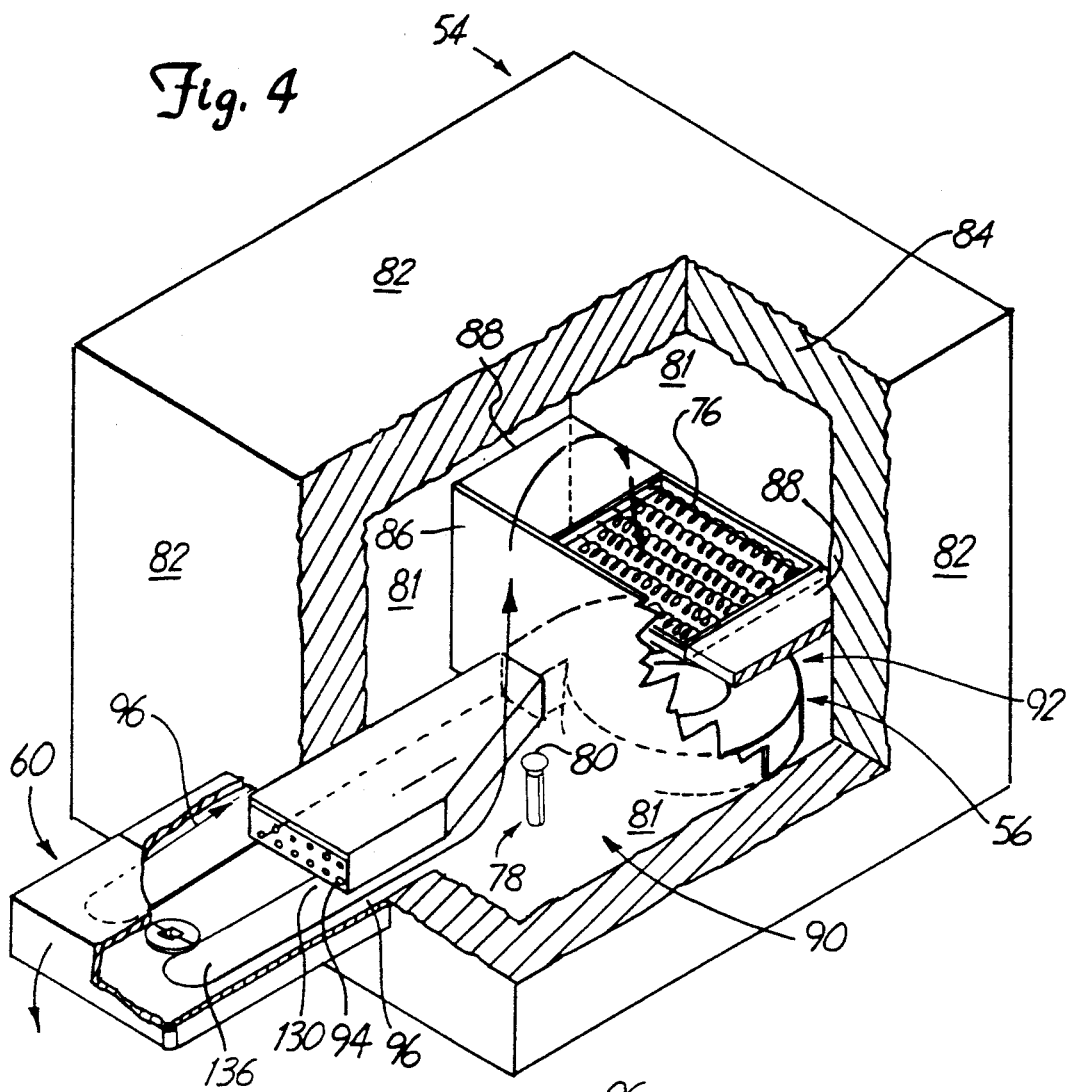
FIG. 4 is a perspective, sectional view of the environmental chamber.

Referring to FIG. 4, the fan section 54 has heating elements 76, such as resistive coils, mounted above the fan 56 to heat the air. Cooling operation of the chamber 12 is through liquid nitrogen introduced into the fan section 54 through an inlet port 78. An atomizing orifice 80 attached to an end of the inlet port 78 allows rapid vaporization of the liquid nitrogen in the fan section 54 to remove heat from the air.

The fan section 54 is larger than the test chamber housing 60 and has inner walls 81, preferably formed from stainless steel, and outer walls 82. Suitable insulation 84, such as high temperature fiberglass insulation, located between the inner and outer walls of the enclosure minimizes heat loss to or from the ambient surrounding air. The fan section 54 includes a deflection plate 86 extending between the inner side walls 81 and attached to the lower inner wall. The deflection plate 86 with the heating elements 76 and separate side panels 88,88 separate the inner chamber of fan section 54 into two portions 90 and 92. The portion 92 includes the fan 56. The deflection plate 86 forces air returning from the test chamber housing 60 over the upper edge of the deflection plate 86 and by the heating elements 76, when heating of the air is desired. The air is then subsequently drawn into the fan 56 and recirculated back to the test chamber housing 60. A pressure relief valve 93, illustrated in FIG. 1, opens to the chamber portion 90 and allows ventilation of the environmental chamber 12 in the event the pressure exceeds a preselected threshold.

Referring back to FIG. 4, the fan section 54 is connected to the test chamber housing 60 through passageways or ducts 94 and 96. Air from the fan 56 is forced into the test chamber housing 60 through the passageway 94, while air exiting the test chamber housing 60 and returning to the fan section 54 travels through the side passageways 96. Preferably, the passageway 94 is located between the passageways 96 in order to minimize heat loss to the ambient environment. For example, when the environmental chamber 12 is heating the test portion 34 of the test specimen 14 to a desired temperature, the air traveling through the passageway 94, having been previously heated by the heating elements 76, is at a temperature higher than the air returning from the test chamber housing 60 through the side passageways 96. The side passageways 96 thus partially insulate the air traveling in the passageway 94 from the cooler inner side walls 81.

Figure 5:
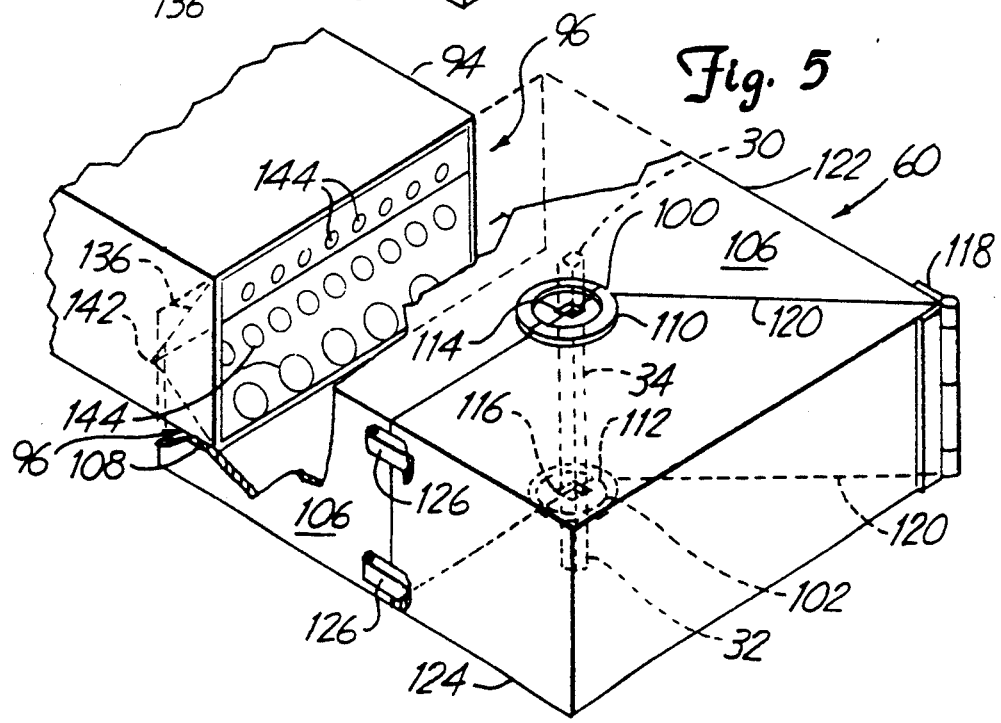
FIG. 5 is a perspective view of the test chamber housing.

Referring to FIGS. 2 and 5, the test chamber housing 60 is secured to the fan section 54 with suitable bolts 97 passing through apertures 99 in support 101. Support 101 is mounted to the housing outer walls 106. The test chamber housing 60 further includes an upper aperture 100 and a lower aperture 102. The specimen 14 to be tested extends through both the upper aperture 100 and the lower aperture 102 leaving end portions 30 and 32 outside the chamber housing where the upper grip 20 and the lower grip 16 are attached. As explained above, the test specimen 14 has a testing portion 34 that is within the test chamber housing 60 and exposed to the forced air provided from the passageway 94. Preferably, the test chamber housing 60, like the fan section 54, is made from stainless steel inner walls 105 and outer walls 106 with an insulation material 108 located between the inner walls 105 and the outer walls 06. However, since the test chamber housing 60 is to be located between the upper grip 20 and the lower grip 16, and in order to maximize the available size of the test chamber housing 60, the insulation material 108 is relatively thin such as, for example, a dense ceramic insulation board.

The upper aperture 100 and the lower aperture 102 have inserts 110 and 112, respectively, each having apertures 114 and 116, respectively, that correspond generally to the sectional profile of the test specimen 14 taken substantially parallel to the upper wall and the lower wall of the test chamber housing 60. The inserts 110 and 112 are replaceable with the apertures 114 and 116 formed therein easily shaped to the sectional profile of the respective portions of the test specimen 14. The inserts 110 and 112 are formed from polytetrafluoroethylene (Teflon). Preferably, when high operating temperatures are expected in the test chamber housing 60, the inserts 110 and 112 are also insulative and then are formed from a material such as a dense ceramic insulation board that is easily machineable.

Figure 7:
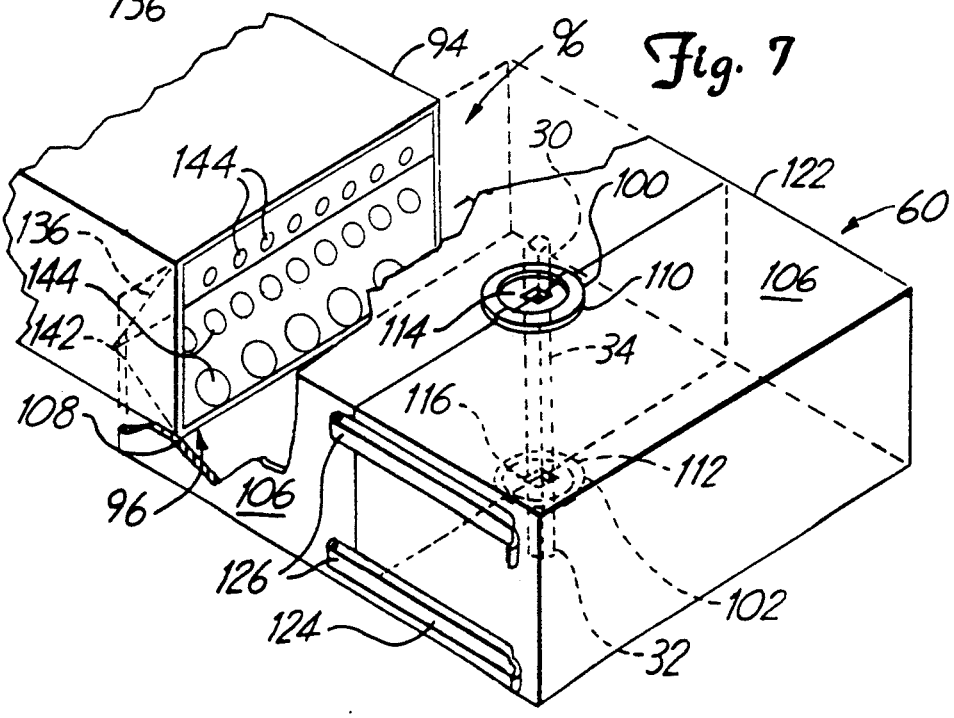
FIG. 7 is a perspective view of the test chamber housing with alternative latching devices.

As further illustrated in FIGS. 5 and 7, the test chamber housing 60 is separable in order to allow access to the test portion 34 of the test specimen 14. In the embodiment illustrated in FIG. 5, the test chamber housing 60 includes a corner hinge 118 fastened to an outer side wall and the front wall of the test chamber housing 60. The hinge line or plane 120 separating the stationary portion 122 of the test chamber housing 60 from the movable portion 124 extends diagonally from the hinge 118 toward the apertures 100 and 102. The hinge plane 120 then extends from the apertures 100 and 102 laterally through the test chamber housing 60 toward the side wall opposite from hinge 118 in order to substantially include the longitudinal axis of the test specimen 14. As illustrated, the hinge plane 120 bisects the upper aperture 100, the lower aperture 102 and their corresponding inserts 110 and 112. Fastening devices 126, such as latches, releasably secure the movable portion 124 to the stationary portion 122.

Alternatively, as illustrated in FIG. 7, four latches 126 (two of which are shown with two similar latches used on the opposite side wall) can be fastened to the side walls of the test chamber 60. The hinge plane 120 would then extend laterally through the test chamber housing 60 again bisecting the upper aperture 100, the lower aperture 102 and their corresponding inserts 110 and 112.

In operation, the environmental chamber 12 maintains the test portion 34 of the test specimen 14 substantially at a selected or desired temperature as follows. Referring to FIGS. 2 and 4 and assuming heating operation of the environmental chamber 12, the air is forced from the fan 56 through the passageway 94 toward the test chamber housing 60. At an outlet end 130 of the passageway 94, the heated air enters the test chamber housing 60 striking the test portion 34 of the test specimen 14 heating it and the surrounding cavity. Air flow diverters 132, illustrated in FIG. 3, attached to the inner wall of moveable section 124 of the test chamber housing 60 smoothly divert air from the passageway 94 to the side passageways 96 to minimize turbulence and/or stagnant air in the test chamber housing 60. The air returning through the side passageways 96 from the test chamber housing 60 to the fan section 54 enters the chamber portion 90 wherein the air strikes the deflection plate 86 creating turbulence, which generally remixes the air. This cooler air then passes over the upper edge of the deflection plate 86 and by the heating elements 76 whereupon it is reheated and drawn back in the fan 56.

Figure 6:
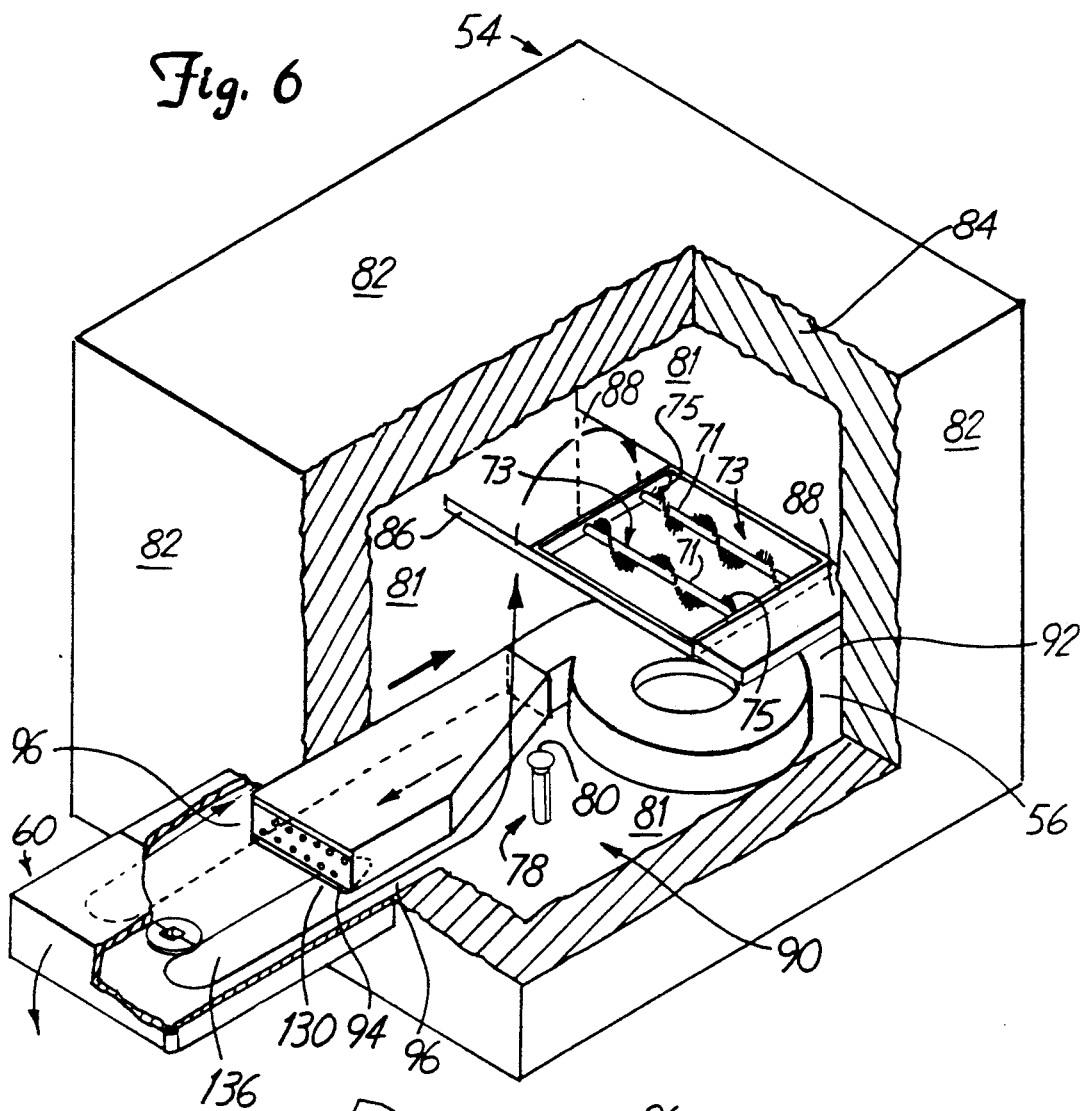
FIG. 6 is a perspective, sectional view of the environmental chamber having an alternative heating source.

FIG. 6 illustrates an alternative embodiment having a different heating source. In this embodiment, the heating means comprises heating elements 73 having a ceramic core 71 and a spirally wound heating element 75. Such heaters are available from Convectronics of Methuen, Mass. When heating elements 73 are used, deflection gate 86 is not necessary for a sufficient amount of air will be heated before entering fan 56.

When operated to cool the test portion 34 substantially below the ambient surroundings to a selected temperature, the air flow through the environmental chamber 12 is as previously described during heating operation. However, the heating elements 76 or 73 are turned off and cooling means such as a conventional mechanical heat exchanger or evaporator is provided. Alternatively, as stated above, liquid nitrogen can be injected into the environmental chamber 12 through the port 78 having the atomizing orifice 80, as is well known in the field.

With the test specimen 14 having end portions 30 and 32 extending through the upper aperture 100 and the lower aperture 102, respectively, and with the center test portion 34 heated or cooled to a desired temperature, a natural temperature gradient following generally known thermodynamic principles can exist from the center portion 34 to each of the end portions 30 and 32. If this temperature gradient is large and thus unacceptable, compensation is provided in order to achieve a minimal, acceptable temperature gradient throughout the longitudinal length of the test portion 36. Temperature gradient compensation is provided by adjusting the air velocity, or alternatively stated, the amount of air striking each area of the test portion 34 along its longitudinal length. The air velocity is adjusted by a baffle 136 that is joined to the environmental chamber 12 in the path of air flow from the blower 56 to the test portion 34, for example, at the outlet end 130 of the passageway 94.

Referring to FIGS. 2 and 5, the baffle 136 is located between support 101 and the fan section outer housing wall 82 using bolts 97. The baffle 136 is wedge-shaped having an upper deflecting surface 138 and a lower deflecting surface 140. The upper deflecting surface 138 is joined to the lower deflecting surface 140 along a leading edge 142, which faces in direction toward the forced air from the fan 56, and which is positioned to substantially correspond to the center area of the test portion 34. The upper surface 138 and the lower surface 140 each have openings 144 therein, which allow a portion of the forced air traveling through the passageway 94 from the fan 56 to pass through the baffle 136 and strike corresponding portions of the test portion 34. However, as further illustrated in FIGS. 2 and 5, the openings 144 are preferably of increasing diameter from the leading edge 142 along the upper surface 138 and the lower surface 140. Increasing opening diameters along the baffle surfaces and the generally wedge-shape of the baffle 136 causes more air to divert to the test specimen areas adjacent the apertures 100 and 102 of the test chamber housing 60, which transfers more heat to these areas of the test portion 34, and thus compensates for heat loss through the end portions 30 and 32. The size of the openings and the extent of deflection along the upper surface 138 and the lower surface 140 of the baffle 136 are chosen so that the desired temperature gradient along the test portion 34 is obtained. Preferably, the air velocity is adjusted such that the air velocity decreases continuously from areas of the test portion 34 adjacent the apertures 100 and 102 of the test chamber housing toward the center area of the test portion 34.

Although the temperature gradient for the longitudinal length of the test portion 34 is dependent upon several factors or parameters including the average temperature desired on the test portion, the thermal conductivity of the test portion, and the air temperature and average air velocity from the fan 56, temperature gradient compensation is provided by the relative difference in velocities of the air striking or passing by the test portion 34. Generally, the difference in velocities is caused by the position of the baffle 136 with respect to the test portion 34 as well as the its overall configuration. For instance, although the baffle 136 was described above with openings 144 and as being located in the passageway 94, when a test specimen is formed from certain materials, a baffle having no openings and attached to the test chamber housing 60 between the passageway opening 130 and the test portion 34 may be needed to obtain the necessary difference in air velocities. In addition, the baffle 136 and the test chamber housing 60 can be interchangeable with corresponding components having different sizes in order to accommodate test specimens of different lengths.

In summary, the environmental chamber of the present invention provides a forced gas or convection assembly that can maintain a selected test portion of a test specimen at temperatures substantially greater than or less than the ambient surroundings. The environmental chamber heats or cools only the test portion of the test specimen, maintaining the desired temperature along the longitudinal length of the test portion within desired temperature gradient limits. With the test specimen having portions extending outwardly from the test chamber housing, the need for expensive test specimen holding assemblies, capable of operating in extreme temperature conditions is eliminated, thereby substantially reducing the cost associated with properly testing materials.

Although the present invention has been described with reference to preferred embodiments, workers skilled in the art will recognize that changes may be made in form and detail without departing from the spirit and scope of the invention.

What is claimed is:

1. A gas convection assembly for maintaining a desired temperature on a test portion of a test specimen, the test specimen mounted at opposite ends on support members for loading along a longitudinal axis, the assembly comprising:
    a housing having a chamber defined by bounding walls, wherein the chamber is accessible through apertures in the housing, and wherein the housing is positioned relative to the test specimen such that the apertures are on the longitudinal axis with the test portion located in the chamber and with end portions of the test specimen extending out the apertures;
    means connected to the housing for forcing a gas into the chamber, the gas maintaining the test portion at the desired temperature; and
    means for adjusting the velocity of the gas striking different areas of the test portion.

2. The assembly as specified in claim 1 wherein the means for adjusting the gas velocity comprises baffling means joined to the housing for adjusting the velocity of gas striking different areas of the test portion.

3. The assembly as specified in claim 2 wherein the baffling means adjusts the gas velocity such that the amount of the gas striking areas of the test portion adjacent the first and second apertures is greater than a center area of the test portion.

4. The assembly as specified in claim 3 wherein the gas striking the test portion decreases continuously from areas of the test portion adjacent the first and second apertures toward the center area of the test portion.

5. The assembly as specified in claim 1 wherein the apertures comprise a first aperture shaped generally to correspond to a peripheral shape of the test specimen aligned with the first aperture, and a second aperture shaped generally to correspond to a peripheral shape of the test specimen aligned with the second aperture.

6. The assembly as specified in claim 5 wherein the first and second apertures are located in replaceable wall portions of the bounding walls of the chamber.

7. The assembly as specified in claim 1 wherein the housing has a first portion separable from a second portion to allow access to the test portion.

8. The assembly as specified in claim 7 wherein the first portion and the second portion separate along a plane extending through the first and second apertures.

9. The assembly as specified in claim 1 wherein the means for forcing gas into the chamber comprises a fan located in a second chamber portion of the housing, the fan substantially recirculating the gas between the first mentioned chamber and the second chamber portion through a passageway between the first mentioned chamber and the second chamber portion.

10. The assembly as specified in claim 9 wherein the passageway between the first mentioned chamber and the second chamber portion comprises a first passageway for gas entering the first mentioned chamber located between passageway for gas exiting the first mentioned chamber.

11. The assembly as specified in claim 1 wherein the means for forcing gas into the chamber comprises a fan driven by a substantially thermally isolated drive.

12. The assembly as specified in claim 11 wherein the drive comprises a motor that is substantially thermally isolated by a drive shaft connected between the fan and the motor.

13. A gas convection assembly for maintaining a desired temperature gradient on a test portion of a test specimen, the test specimen being mounted on support members at opposite ends of the test specimen, which support members are adapted for applying force loads to the test specimen relative to a longitudinal axis of the test specimen, the assembly comprising:
    a housing having a first chamber and a second chamber, the first chamber defined by an upper wall, a lower wall and a pair of spaced side walls extending between the upper and lower walls, wherein the first chamber is accessible through upper and lower apertures in the housing, and wherein the housing is positioned relative to the test specimen such that the apertures are on the longitudinal axis with the test portion located in the first chamber and a first end portion of the test specimen extending out the upper aperture and a second end portion extending out the lower aperture;
    a passageway connecting the first and second chambers;

fan means located in the second chamber for recirculating gas between the first chamber and the second chamber through the passageway; and baffling means joined to the housing in the path of gas travel from the fan means to the test portion, the baffling means adjusting the velocity of gas passing by selected areas of the test portion to obtain the desired temperature gradient.

14. The assembly as specified in claim 13 wherein the baffling means is located on an outlet end of the passageway for gas entering into the first chamber.

15. The assembly as specified in claim 14 wherein the baffling means adjusts the gas velocity passing by the test portion such that the gas velocity by areas of the test portion adjacent the apertures is greater than a center area of the test portion.

16. The assembly as specified in claim 15 wherein the gas velocity by the test portion decreases continuously from areas of the test portion adjacent the apertures toward the center area of the test portion.

17. The assembly as specified in claim 16 wherein the passageway between the first chamber and the second chamber comprises a first passageway for gas entering the chamber located between passageways for gas exiting the chamber.

18. The assembly as specified in claim 13 wherein the upper aperture is shaped generally to correspond to the sectional profile of the test specimen taken substantially parallel to the upper wall, and the lower aperture is shaped generally to correspond to the sectional profile of the test specimen taken substantially parallel to the lower wall.

19. The assembly as specified in claim 18 wherein the apertures are located in replaceable wall portions of the upper and lower walls.

20. A gas convection assembly for maintaining a desired temperature on a test portion of a test specimen, the test specimen mounted at opposite ends on support members for loading along a longitudinal axis, the assembly comprising:

a housing having a first chamber an a second chamber defined by bounding walls, wherein the first chamber is accessible through apertures in the housing, and wherein the housing is positioned relative to the test specimen such that the apertures are on the longitudinal axis with the test portion located in the first chamber and with end portions of the test specimen extending out the apertures;

means for substantially recirculating the gas between the first chamber and the second chamber through a first passageway for gas entering the first chamber, the first passageway located between a set of passageways for gas exiting the first chamber, the gas maintaining the test portion at the desired temperature, whereby the recirculating means is a fan positioned in the second chamber.

* * * * *

UNITED STATES PATENT AND TRADEMARK OFFICE
CERTIFICATE OF CORRECTION

PATENT NO. : 5,302,023
DATED : April 12, 1994
INVENTOR(S) : Larsen et al.

It is certified that error appears in the above-indentified patent and that said Letters Patent is hereby corrected as shown below:

Title page, item 75, delete "Bryon" and insert --Byron--.

Column 8, line 38, cancel "passageway" and insert --passageways--.

Column 10, line 12, cancel "an" and insert --and--.

Signed and Sealed this

Twenty-third Day of August, 1994

Attest:

BRUCE LEHMAN

*Attesting Officer*     *Commissioner of Patents and Trademarks*